United States Patent [19]

Ford

[11] Patent Number: 5,712,129
[45] Date of Patent: Jan. 27, 1998

[54] RAPAMYCIN DERIVATIVE WITH ANTIMICROBIAL, ANTICANCER AND IMMUNOMODULATION ACTIVITY

[75] Inventor: Brian Douglas Ford, Forest Green, England

[73] Assignee: SmithKline Beecham p. l. c., Brentford, England

[21] Appl. No.: 591,457

[22] PCT Filed: Jul. 25, 1994

[86] PCT No.: PCT/GB94/01600

§ 371 Date: Jan. 31, 1996

§ 102(e) Date: Jan. 31, 1996

[87] PCT Pub. No.: WO95/04060

PCT Pub. Date: Feb. 9, 1995

[30] Foreign Application Priority Data

Jul. 31, 1993 [GB] United Kingdom ............ 9315914

[51] Int. Cl.$^6$ ............ C12P 17/18; C12R 1/465; A61K 31/455; C07D 498/18
[52] U.S. Cl. ............ 435/118; 435/253.5; 540/456; 514/291
[58] Field of Search ............ 540/456; 514/291; 435/118, 253.5

[56] References Cited

U.S. PATENT DOCUMENTS

| | | | |
|---|---|---|---|
| 5,256,790 | 10/1993 | Nelson | 514/291 |
| 5,310,901 | 5/1994 | Parsons et al. | 540/456 |
| 5,310,903 | 5/1994 | Goulet et al. | 540/456 |

FOREIGN PATENT DOCUMENTS

| | | | |
|---|---|---|---|
| 514144 | 11/1992 | European Pat. Off. | 540/456 |
| 0 593 227 | 4/1994 | European Pat. Off. | 540/456 |
| 1 436 447 | 5/1976 | United Kingdom | 540/456 |

*Primary Examiner*—Robert T. Bond
*Attorney, Agent, or Firm*—Yuriy P. Stercho; Stephen A. Venetianer; Edward T. Lentz

[57] ABSTRACT

A compound of formula (I) is obtainable by the cultivation of a genus Streptomyces, such as Streptomyces NCIMB 40515, in the presence of rapamycin, and recovery thereof from the culture medium. The compound, and pharmaceutical compositions containing it, is useful as an immunomodulatory agent as an anticancer agent, or in the treatment of microbial infections in animals including humans.

4 Claims, No Drawings

RAPAMYCIN DERIVATIVE WITH ANTIMICROBIAL, ANTICANCER AND IMMUNOMODULATION ACTIVITY

This application is a 371 of PCT/GB 94/01600, filed 25 Jul. 1994, which claims priority of British Application 9315914.3 filed 31, Jul. 1993.

The present invention relates to a novel compound and derivatives to processes for their production, to pharmaceutical formulations containing them, to their use in medical therapy, particularly in the treatment of microbial infections, and also to their use as immuno modulatory agents.

Rapamycin a known compound and was first isolated as an extract of the fungus *Streptomyces hygroscopicus* and reported to have antifungal activity (British Patent 1436447). Subsequently rapamycin has been implicated as an immunosuppressant (Martel R. R. et al Can. J. Physiol. Pharmacol, 55, 48–51, 1977).

A large number of microorganisms have been found to produce a variety of compounds which have subsequently been isolated and have been shown to possess useful therapeutic properties. Novel compounds have also been obtained by the incubation or cultivation of a microorganism in the presence of known compounds. One such new compound is 42-O-demethylrapamycin. This novel compound has been found to have useful antimicrobial and anticancer and immunomodulation activity.

Accordingly the present invention provides 42-O-demethylrapamycin and derivatives thereof.

The invention in a second aspect, further provides a process for the production of 42-O-demethylrapamycin which comprises contacting a micoorganism with rapamycin and subsequently isolating 42-O-demethylrapamycin or derivatives thereof from the incubation.

42-O-demethylrapamycin is believed to have the structure shown in formula (I):

i) it has an apparent molecular weight of 899 by fast atom bombardment (FAB) mass spectroscopy;

ii) it is obtainable by the cultivation of a microorganism from the genus Streptomyces, in the presence of rapamycin and the recovery of 42-O-demethylrapamycin or a derivative thereof from the culture medium;

iii) $^{13}$CNMR spectroscopy reveals 50 carbons in the molecule;

iv) it shows antifungal activity;

v) it shows immunomodulatory activity.

The term 'cultivation' (and derivatives of that term) as used herein means the deliberate aerobic growth of an organism in the presence of assimilable sources of carbon, nitrogen, sulphur and mineral salts. Such aerobic growth may take place in a solid or semi-solid nutritive medium, or in a liquid medium in which the nutrients are dissolved or suspended. The cultivation may take place on an aerobic surface or by submerged culture. The nutritive medium may be composed of complex nutrients or may be chemically defined.

It has been found that suitable microorganisms for use in the process according to the invention include bacterial strains belonging to the genus *Streptomyces* which are capable of elaborating 42-O-demethylrapamycin. It has further been found that an example of such a strain is sp. NCIMB 40515, which has been isolated from nature and also mutants thereof.

The term 'mutant' as used herein includes any mutant strain which arises spontaneously or through the effect of an external agent whether that agent is applied deliberately or otherwise. Suitable methods of producing mutant strains including those outlined by H. I. Adler in 'Techniques for the Development of Microorganisms' in 'Radiation and Radioisotopes for Industrial Microorganisms', Proceedings of a Symposium, Vienna, 1973, page 241, International Atomic Energy Authority, and these include:

(i) Ionizing radiation (e.g. X-rays and γ-rays), u.v. light, u.v. light plus a photosensitizing agents (e.g.

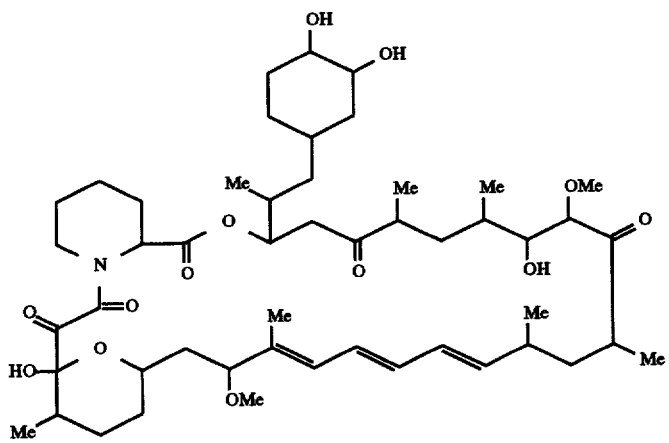

(I)

This compound is referred to herein as 42-O-demethylrapamycin according to the numbering system of J. Findlay et al., Can. J. Chem. (1980) 58, 579. However according to the more recent numbering system of J. Mc Alpine et al., J. Antibiotics (1991) 44. 688 this would be known as 39-O-demethylrapamycin.

Following the numbering system according to Chemical Abstracts (11th Cumulative Index 1982–86 page 60719CS), the compound of the present invention would be called 41-O-demethylrapamycin.

The compound in formula (I) has the following characteristics:

8-methoxypsoralen), nitrous acid, hydroxylamine, pyrimidine base analogues (e.g. 5-bromouracil), acridines, alkylating agents (e.g. mustard gas, ethyl-methane sulphonate), hydrogen phenols, formaldehyde, heat, and (ii) Genetic techniques, including, for example, recombination, transformation, transduction, lysogenisation, lysogenic conversion, protoplast fusion and selective techniques for spontaneous mutants.

Using the methods of Becker B. Lechevalier M. P., Gordon R. E., Lechevalier H. A., 1964, Appl. Microbiol. 12, 421–423 and Williams S. T., Goodfellow M, Wellington E. M. H., Vickers J. C., Alderson. G., Sneath P. H. A., Sackin M. J., and Mortimer M. 1983 J. Gen. Microbiol. 129, 1815–1830, Sp. NCIMB 40515 has been identified as a previously unreported, atypical, strain of Streptomyces and therefore also forms a part of the present invention, particularly in biologically pure form. It has been deposited at the National Collections of Industrial and Marine Bacteria Ltd. (N.C.I.M.B), Aberdeen, Scotland under number NCIMB 40515 on 7th Jul. 1992.

The medium for cultivating sp. NCIMB 40515 suitably contains sources of assimilable carbon and assimilable nitrogen together with inorganic salts. Suitable sources of nitrogen include yeast extract, soyabean flour, meat extract, cottonseed, flour, malt, distillers dried solubles, amino acids, protein hydrolysates and ammonium and nitrate nitrogen. Suitable carbon sources include glucose, lactose, maltose, starch and glycerol. Suitably the culture medium also includes alkali metal ions (for example, sodium) halogen ions (for example, chloride), and alkaline earth metal ions (for example calcium and magnesium), as well as trace elements such as iron and cobalt.

The cultivation may suitably be effected at a temperature of about 20° to 35° C., advantageously 20° to 30° C., and the culture may suitably be contacted with rapamycin for up to 7 days, advantageously about 3 to 5 days, in order to give an optimum yield of the desired product after isolation for example as described below.

The desired product or a derivative thereof may be isolated from the culture medium and worked up and purified using conventional techniques for such compounds. All such isolation and purification procedures may conveniently be effected at cool to ambient temperature, for example at a temperature within the range of from 4° to 40° C., conveniently from 20° to 35° C.

The desired compound may readily be identified in a routine manner by testing for biological activity and/or by monitoring the h.p.l.c. retention time.

Suitably, the separation procedure may include a high-performance liquid chromotography step, preferably as the last step. Elution may be effected using aqueous methanol.

42-O-demethylrapamycin and its derivatives may be crystalline or non-crystalline and, if crystalline, may optionally be hydrated or solvated.

The derivatives are preferably pharmaceutically acceptable derivatives. Derivatives may include salts, with pharmaceutically acceptable counter ions.

The compounds according to the invention are suitably provided in substantially pure form, for example at least 50% pure, suitable at least 60% pure, advantageously at least 75% pure, preferably at least 85% pure, preferably at least 95% pure, especially at least 98% pure, all percentages being calculated as weight/weight. An impure or less pure form of a compound according to the invention may, for example, be used in the preparation of a more pure form of the same compound or of a related compound (for example a corresponding derivative) suitable for pharmaceutical use.

42-O-demethylrapamycin and its pharmaceutically acceptable derivatives have antifungal activity and are useful for the prophylactic and therapeutic treatment of fungal infections in animals, especially mammals including humans, in particular humans and domesticated animals (including farm animals). The compounds may be used for the treatment of topical fungal infections in man caused by, among other organisms, species of Candida (eg *Candida Albicans*), Trichophyton (eg *Trichophyton mentagrophytes*), Microsporum (eg *Microsporum gypseum*) or Epidermophyton or in mucosal infections caused by *Candida Albicans* (e.g. thrush and vaginal candidiasis). They may also be used in the treatment of systemic fungal infectious caused by, for example *Candida albicans, Cryptococcus neoformans, Aspergillus fumigatus,* Coccidiodes, Paracocciciodes, Histoplasma or *Blasmtomyces spp.* They may also be of use in treating eumycotic mycetoma, chromoblastomycosis and phycomycesis.

42-O-demethylrapamycin and its pharmaceutically acceptable derivatives are also active as an immunomodulatory agents. The term "immunomodulatory agent" as used herein means that the compound of the invention is capable of inducing immune suppression by inhibiting T (and B) cell responses in vitro and/or by producing a statistically significant decrease in the intimation system response medicated secondary lesion in the adjuvant induced arthritis. Indications for therapy include, but are not limited to, the treatment of the following disease states: rheumatoid arthritis, systemic lupus erythematosis, multiple sclerosis, acute transplantation/graft rejection, myasthenia gravis, progressive systemic sclerosis, multiple myeloma, atopic dermatitis, hyperimmunoglobulin E, hepatitis B antigen negative chronic active hepatitis, Hashimoto's thyroiditis, Familial Mediterranean fever, Grave's disease, autoimmune hemolytic anemia, primary biliary cirrhosis, inflammatory bowel disease, insulin dependent diabetes mellitus.

42-O-demethylrapamycin and its pharmaceutically acceptable derivatives should also have activity against carcinogenic tumours. More specifically, the compounds should be useful for reducing tumour size, inhibiting tumour grown and/or prolonging the survival time of turnout-bearing animals.

Accordingly the invention provides 42-O-demethylrapamycin or derivatives thereof for use in medical therapy, in particular for use as an antifungal agent or immunomodulatory agent, or as an agent against carcinogenic tumours.

The invention further provides a method of treating a human or animal suffering from a fungal infection by the administration of an effective amount of 42-O-demethylrapamycin or derivative thereof.

Moreover, the invention provides a method of treating a human or animal in need of immunomodulation by administration of an effective mount of 42-O-demethylrapamycin or derivative thereof.

The invention also provides a method of treating carcinogenic tumours in a human or animal comprising administering to such human or animal an effective, non-toxic amount of 42-O-demethylrapamycin or derivative thereof.

The invention further provides a pharmaceutical composition comprising a compound of the formula (I) or a pharmaceutically acceptable salt thereof together with a pharmaceutically acceptable diluent or carrier. The composition is preferably for human use in tablet, capsule, injectable or cream form.

For human use 42-O-demethylrapamycin or derivatives thereof can be administered alone, but will generally be administered in admixture with a pharmaceutical carrier selected with regard to the intended route of administration and standard pharmaceutical practice. For example, they may be administered orally in the form of a tablet containing such excipients as starch or lactose, or in a capsule or ovule either alone or in admixture with excipients, or in the form of an elixir or suspension containing a flavouring or colouring agent. They may be injected parenterally, for example, intravenously, intramuscularly or subcutaneously. For parenteral administration, they are best used in the form of a sterile solutions which may contain other substances, for example, enough salts or glucose to make the solution isotonic.

For oral and parenteral administration to human patients suffering from a fungal infection, it is expected that the daily dosage level of the antifungal compounds of formula (I) will be from 0.05 to 100 preferably 0.1 to 10 mg/kg (in divided doses) when administered by either the oral or parenteral route. Thus tablets or capsules of the compounds can be expected to contain from 5 mg to 0.5 g of active compound for administration singly or two or more at a time as appropriate. The physician in any event will determine the actual dosage which will be most suitable for an individual patient and will vary with the age, weight and response of the particular patient. The above dosages are exemplary of the average case. There can, of course, be individual instances where higher or lower dosage ranges are merited, and such are within the scope of this invention.

Equally for a human patient in need of immunomodulation the daily parenteral or oral dosage regimen for the compound or derivative thereof will preferably be from 0.1 mg/kg to 30 mg/kg.

One skilled in the art would be able, by routine experimentation, to determine what an effective, non-toxic amount of compound or derivative thereof would be for the purpose of treating carcinogenic tumours. Generally, however, an effective dosage is expected to be in the range of about 0.05 to 100 milligrams per kilogram body weight per day.

No unacceptable toxicological effects are expected when the compound is administered in the above mentioned dosage ranges.

The compounds and compositions according to the invention may be formulated for administration in any convenient way for use in human or veterinary medicine, by analogy with other antifungal, anticancer or immunomodulatory agent.

The compounds and tablets and capsules for oral administration may be in unit dosage form, and may contain conventional excipients including, for example, binding agents, for example, syrup, acacia, gelatin, sorbitol, tragacanth, or polyvinylpyrrollidone; fillers, for example lactose, sugar, maize-starch, calcium phosphate, sorbitol or glycine; tabletting lubricants, for example magnesium stearate, talc, polyethylene glycol or silica; disintegrants, for example potato starch; and pharmaceutically acceptable wetting agents, for example sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or another suitable vehicle before use. Such liquid preparations may contain conventional additives, including, for example, suspending agents, for example sorbitol, methyl cellulose, glucose syrup, gelatin, hydroxyethyl cellulose, carboxymethyl cellulose, aluminium stearate gel or hydrogenated edible fats; emulsifying agents, for example lecithin, sorbitan monooleate or acacia; non-aqueous vehicles (which may include edible oils), for example almond oil, oily esters (for example glycerine), propylene glycol, or ethyl alcohol; preservatives, for example methyl or propyl p-hydroxybenzoate or sorbic acid; and, if desired, conventional flavouring and colour agents.

Compositions according to the invention intended for topical administration may, for example, be in the form of ointments, creams, lotions, eye ointments, eye drops, ear drops, impregnated dressings, and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

Compositions according to the invention may be formulated as suppositories, which may contain conventional suppository bases, for example cocoa-butter or other glycerides.

Compositions according to the invention intended for parenteral administration may conveniently be in fluid unit dosage forms, which may be prepared utilizing the compound and a sterile vehicle, propyleneglycol. The compound, depending on the vehicle and concentration used, may be either suspended or dissolved in the vehicle. Parenteral suspensions may be prepared in substantially the same manner except that the compound is suspended in the vehicle instead of being dissolved and sterilisation cannot be accomplished by filtration. The compound may instead be sterilised by exposure to ethylene oxide before being suspended in the sterile vehicle. Advantageously, a surfactant or wetting agent is included in such suspensions in order to facilitate uniform distribution of the compound.

Compositions according to the invention may also be administered by inhalation. By "inhalation" is meant intranasal and oral inhalation administration. Appropriate dosage forms for such administration such as an aerosol formulation or a metered dose inhaler, may be prepared by conventional techniques.

The following examples serve to illustrate the present invention.

EXAMPLE 1

Preparation of 42-O-demethylrapamycin

A culture capable of producing 42-O-demethylrapamycin from rapamycin has been classified as *Streptomyces sp.* and has been deposited in the National Collection of Industrial and Marine Bacteria, 23, St. Machar Drive, Aberdeen AB2 1RY, Scotland, UK. under the accession number NCIMB 40515.

Cultivation

Each of five 500 ml flasks containing 100 ml M2 medium [arkasoy, 10 g/l; glycerol, 20 g/l; $CoCl_2.6H_2O$, 0.005 g/l; $MgCl_2.2H_2O$, 0.1 g/l; $FeCl_3$, 0.03 g/l; $ZnCl_2$, 0.005 g/l; $CuCl_2.2H_2O$, 0.005 g/l; $MnSO_4.4H_2O$, 0.005 g/l pH 6.6 unadjusted] were inoculated with 2 plugs of agar from well growing cultures on A3 agar [yeast extract, 5 g/l; malt extract, 10 g/l; glycerol, 10 g/l; peptone soya, 5 g/l; agar No.3, 20 g/l; pH 6.5] in petri dishes. Alternatively a large loopful of well growing culture from a petri dish was mixed with 3 ml of Tween 80 and the total contents added to 100 ml M2 media in a 500 ml flask, grown at 28° C., 240 rpm for 3 days, 1 ml of the culture broth is then used to inoculate 100ml M2 media in each of the five 500 ml flasks. The flasks were then grown at 28° C. and 240 rpm.

Incubation

After 5 days, rapamycin (20 mg) as a solution in acetone (3.5 ml) was added to each flask. Rapamycin can be obtained from a rapamycin-producing culture NCIMB 40319 deposited on 14 Sep. 1990, or by culturing a rapamycin producing organism eg NRRL 5491 as disclosed in U.S. Pat. No. 3,929,992 issued 30 Dec. 1975, the entire disclosure of which is hereby incoporated by reference. Flasks were incubated at 28° C., 240 rpm for about 20 h.

Isolation procedure

Solvent extraction

The contents of the flasks was bulked and adjusted to pH4 with dilute sulphuric acid. 500 ml of dichloromethane was added and the mixture stirred for 2 h, the organic solvent phase was recovered separating the phases by centrifugation and a further 200 ml of dichloromethane added and stirred for 1 h. The organic solvent phases were combined and concentrated in vacuo to an oil. To the oil was added 100 ml methanol, the methanol extract filtered and the filtrate concentrated to an oil in vacuo.

Silica chromatography

The oil was loaded on a Kieselgel 60 (70–230 mesh) column (25×50 mm) packed in acetone:hexane (15:85). After loading, the column was eluted with a step gradient of acetone-hexane. Fractions eluted after 35:65 acetone:hexane contain 42-O-demethylrapamycin. These were combined and reduced to dryness in vacuo and stored at −20° C.

Preparative hplc

The stored solid was dissolved in 500 μl methanol and 100 μl portions injected separately onto a reverse phase Microsorb C-18 column and pre column (21.4 mm×25 cm and 21.4×5 cm) (Rainin Instruments USA). After injection elution continued with 78:22 methanol:$H_2O$, at 6 ml/minute and was monitored for UV absorbance at 278 nm. Fractions containing the object compound from a total of 5 injections were pooled, concentrated in vacuo to remove the methanol and freeze dried.

Fractions containing the object compound were analysed by reverse phase hlpc using a Spherisorb S10ODS2 (PhaseSep) column (25 cm×4.6 mm) and a Waters pre-column. The column was monitored by UV absorption at 278 nm and eluted with 78:22 methanol-water at 2 ml/minute. Under these conditions the object compound had a retention time of 6.8 minutes (differing from rapamycin, retention time of 8.4 minutes).

Spectroscopic Data

The resulting compound was characterised by mass spectroscopy (FAB)[M +Na]$^+$=922 and by proton and $^{13}C$ nuclear magnetic resonance spectroscopy (see Table 1 below). UV spectroscopy shows $UVl_{max}$ in acetone at 275 nm.

TABLE 1

Spectroscopic Data for 42-O-Demethylrapamycin:
MS (FAB/NaCl) m/z 922 (M + Na)$^+$
1H-NMR (CDCl3, 400 MHz, 4:1 mixture of trans: cis amide rotamers; data for the trans-rotamer):

| ppm | assign | muitipl | J's (Hz) |
|---|---|---|---|
| 6.383 | H-4 | dd | 14.7, 10.5 |
| 6.310 | H-3 | dd | 14.7, 9.8 |
| 6.134 | H-2 | dd | 15.0, 9.8 |
| 5.970 | H-5 | d | lo.5 |
| 5.518 | H-1 | dd | 15.0, 9.0 |
| 5.407 | H-26 | d | 10.3 |
| 5.273 | H-20 | d | 5.0 |
| 5.152 | H-22 | q | 5.8 |
| 4.618 | OH-13 | s | — |
| 4.197 | H-28 | br d | 5.0 |
| 3.89 | H-9 | m | — |
| 3.782 | H-29 | d | 5.3 |
| 3.647 | H-7 | t | 7.3 |
| 3.515 | H-16 | br d | 11.9 |
| 3.338 | MeO-29 | s | — |
| 3.4–3.25 overlapping multiplet of H-25, H-42 and H-43 | | | |
| 3.134 | MeO-7 | s | |

TABLE 1-continued

Spectroscopic Data for 42-O-Demethylrapamycin:
MS (FAB/NaCl) m/z 922 (M + Na)$^+$
1H-NMR (CDCl3, 400 MHz, 4:1 mixture of trans: cis amide rotamers; data for the trans-rotamer):

| ppm | assign | muitipl | J's (Hz) |
|---|---|---|---|
| 2.710 | H-23 | dd | 16.8, 5.8 |
| 2.587 | H-23 | dd | 16.8, 5.7 |
| 1.758 | Me-27 | s | — |
| 1.655 | Me-6 | s | — |
| 1.085 | Me-25 | d | 6.7 |
| 1.051 | Me-33 | d | 6.4 |
| 0.985 | Me-31 | d | 6.5 |
| 0.942 | Me-12 | d | 6.6 |
| 0.905 | Me-38 | d | 6.7 |

EXAMPLE 2

Bioactivity of 42-O-demethylrapamycin

The compound was analysed for antifungal and immunosuppressive activity using the following bioassays:

A. Assay for antifungal activity

Yeast organism (Saccharomyces cerevisiae) in logarithmic growth were plated on complete agar medium (YPD). Compounds dissolved in an appropriate aqueous or organic solvent were placed in wells punched in the agar. Plates were incubated for 48 hours and zones of inhibition were measured. The potency of compounds were quantified by regression analysis of plots of inhibition zone versus the log of drug concentration.

B. Mitogenesis Assay for Immunosuppresive Activity

Spleen cells for BDF1 female mice were established in RPMI with 10% fetal calf serum at 5×10$^6$/mL. One hundred mL aliquots of this suspension (5×10$^5$ cells) were dispensed into 96-well round-bottomed microtiter plates (Linbro, Flow Laboratories). Concanavalin A (5 μg/ml) was added as the mitogenic stimulus, and the final volume in the microtiter wells was adjusted to 200 μL with RPMI. Cell cultures were incubated for 72 hours at 37° C. in a 5% $CO_2$ atmosphere and pulsed with 0.5 μCi $^3$H-thymidine (specific activity 2.00 Ci/mole) for the last 18 hours of the 72 hours culture. The cells were harvested on an automated multiple sample harvester and cell-associated radioactivity counted in a Beckman liquid scintillation counter. The results were expressed as the mean values derived from quadruplicate measurements. Cell viability was determined by trypan blue exclusion after 72 hours of incubation. Compounds to be tested were added to the microtiter plates at the appropriate dilutions prior to the addition of cells.

Results of these two assays for compounds of this invention are provided in Table 2.

TABLE 2

| Compound | a Antifungal Activity | b Mitogenesis |
|---|---|---|
| Control (rapamycin) | 0.0061 | 1 ± 1 |
| 42-O-demethylrapamycin | 0.012 | 3 |
| | 0.013 | — | a Assay: (IC$_{12}$, μg/ml)
b Assay: (IC$_{50}$, nM)

EXAMPLE 3

COMPOSITION EXAMPLES A—H

A—CAPSULE COMPOSITION

A pharmaceutical composition of this invention in the form of a capsule is prepared by filling a standard two-piece hard gelatin capsule with 50 mg of a compound of the invention, in powdered form, 100 mg of lactose, 32 mg of talc and 8 mg of magnesium stearate.

B—INJECTABLE PARENTERAL COMPOSITION

A pharmaceutical composition of this invention in a form suitable for administration by injection is prepared by stirring 1.5% by weight of a compound of the invention in 10% by volume propylene glycol and water. The solution is sterilized by filtration.

C—OINTMENT COMPOSITION

Compound of the invention 1.0 g

White soft paraffin to 100.0 g

The compound of the invention is dispersed in a small volume of the vehicle and granually incorporated into the bulk of the vehicle of produce a smooth, homogeneous product. Collapsible metal tubes are then filled with the dispersion.

D—TOPICAL CREAM COMPOSITION

Compound of the invention 1.0 g

Polawax GP 200 20.0 g

Lanolin Anhydrous 2.0 g

White Beeswax 2.5 g

Methyl hydroxybenzoate 0.1 g

Distilled Water to 100.0 g

The polawax, beeswax and lanolin are heated together at 60° C. The compound of the invention is then added and dispersed throughout, and the composition is allowed to cool with slow speed stirring.

E—TOPICAL LOTION COMPOSITION

Compound of the invention 1.0 g

Sorbitn Monolaurate 0.6 g

Polysorbate 20 0.6 g

Cetostearyl Alcohol 1.2 g

Glycerin 6.0 g

Methyl Hydroxybenzoate 0.2 g

Purified Water B.P. to 100.00 ml

The methyl hydroxybenzoate and glycerin are dissolved in 70 ml of the water at 75. The sorbitan monolaurate, polysorbate 20 and cetostearyl alcohol are melted together at 75 C and added to the aqueous solution. The resulting emultion is homogenized, allowed to cool with continuous stirring and the compound of the invention is added as a suspension in the remaining water. The whole suspension is stirred until homogenized.

F—EYE DROP COMPOSITION

Compound of the invention 0.5 g

Methyl Hydroxybenzoate 0.01 g

Propyl Hydrobenzoate 0.04 g

Purified water B.P. to 100.00 ml (B.P.=British Pharmacopia) The methyl and propyl hydroxybenzoates are dissolved in 70 ml purified water at 75° C. and the resulting solution is allowed to cool. The compound of the invention is then added, and the solution is sterilized by filtration through a membrane filter (0.22 mu m pore size) and packed aseptically into suitable sterile containers.

G—COMPOSITION FOR ADMINISTRATION BY INHALATION

For an aerosol container by a capacity of 15–20 ml: Mix 10 mg of a compound of the invention with 0.2–0.2% of a lubricating agent, such as polysorbate 85 or oleic acid, and disperse such mixture in a propellant, such as freon, preferably in a comination of (1,2 dichlorotetrafluoroethane) and difluorochloromethane and put into an appropriate aerosol container adapter for either tranasal or oral inhalation administration.

H—COMPOSITION FOR ADMINISTRATION BY INHALATION

For an aerosol container with a capacity of 15–20 ml; Dissolve 10 mg of a compound of the invention in ethanol (6–8 ml), add 0.1–0.2% of a lubricating agent, such as polysorbate 85 or oleic acid; and disperse such in a propellant, such as freon, preferably a combination of (1.2 dichlorotetrafluoroethane) and difluorochloromethane, and put into an appropriate aerosol container adapter for either intranasal or oral inhalation administration.

I claim:

1. A process for the production of a compound of formula (I):

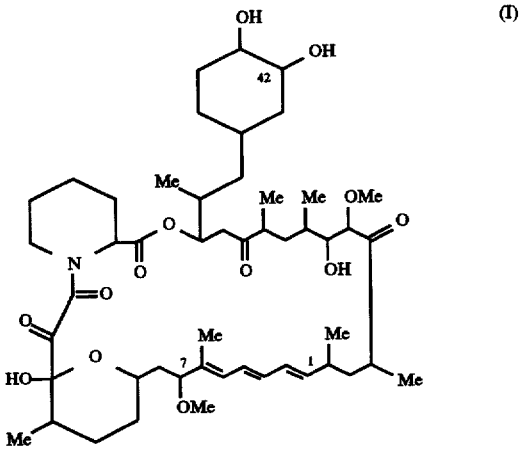

which is 42-O-demethylrapamycin, or pharmaceutically acceptable salt thereof, which comprises contacting a microorganism which belongs to the genus Streptomyces with rapamycin and subsequently isolating said 42-O-demethylrapamycin, or a pharmaceutically acceptable salt thereof, from the incubation.

2. A process according to claim 1, which comprises separating said compound or a pharmaceutically acceptable salt thereof, from a solution thereof in admixture with other antibacterially active substances and/or inactive substance by adsorption onto an adsorbent resin.

3. A process as claimed in claim 1, wherein the producing microorganism is Streptomyces NCIMB 40515.

4. Streptomyces NCIMB 40515.

* * * * *